United States Patent
Kokott et al.

(10) Patent No.: US 8,382,833 B2
(45) Date of Patent: Feb. 26, 2013

(54) SOFT-TISSUE IMPLANT HAVING ANTIBACTERIAL EFFECT

(75) Inventors: Andreas Kokott, Bad Steben (DE); Bettina Hoffmann, Altenkunstadt (DE); Martina Feldmann, Eckersdorf (DE); Günter Ziegler, Nürnberg (DE); Lukas Prantl, Regensburg (DE); Marita Eisenmann-Klein, Regensburg (DE)

(73) Assignee: Biocer Entwicklungs GmbH, Bayreuth (DE)

( * ) Notice: Subject to any disclaimer, the term of this patent is extended or adjusted under 35 U.S.C. 154(b) by 194 days.

(21) Appl. No.: 12/674,105

(22) PCT Filed: Aug. 5, 2008

(86) PCT No.: PCT/DE2008/001310
§ 371 (c)(1),
(2), (4) Date: Mar. 31, 2010

(87) PCT Pub. No.: WO2009/024121
PCT Pub. Date: Feb. 26, 2009

(65) Prior Publication Data
US 2011/0106248 A1 May 5, 2011

(30) Foreign Application Priority Data
Aug. 21, 2007 (DE) .................... 10 2007 039 871

(51) Int. Cl.
*A61F 2/12* (2006.01)
(52) U.S. Cl. .......................................... 623/8
(58) Field of Classification Search ........ 623/1.42–1.48, 623/7–8
See application file for complete search history.

(56) References Cited

U.S. PATENT DOCUMENTS

| | | | |
|---|---|---|---|
| 5,853,745 A * | 12/1998 | Darouiche .................... | 424/423 |
| 6,432,449 B1 * | 8/2002 | Goldenberg et al. ......... | 424/486 |
| 6,475,516 B2 * | 11/2002 | DiCosmo et al. ............. | 424/450 |
| 6,913,626 B2 * | 7/2005 | McGhan .................... | 623/23.73 |
| 7,179,849 B2 * | 2/2007 | Terry ............................ | 523/122 |
| 7,229,413 B2 * | 6/2007 | Violante et al. .............. | 600/458 |
| 7,238,363 B2 * | 7/2007 | Mansouri et al. ............. | 424/423 |
| 7,381,715 B2 * | 6/2008 | Sabesan ......................... | 514/55 |
| 7,713,573 B2 * | 5/2010 | Owens et al. .................. | 427/2.1 |
| 8,057,534 B2 * | 11/2011 | Boismier et al. ............. | 623/1.38 |
| 2002/0018795 A1 * | 2/2002 | Whitbourne et al. ......... | 424/414 |
| 2003/0203003 A1 | 10/2003 | Nelson et al. | |
| 2004/0235161 A1 * | 11/2004 | Tabata et al. .................. | 435/371 |
| 2005/0031664 A1 * | 2/2005 | Vogt et al. ..................... | 424/423 |
| 2006/0024350 A1 * | 2/2006 | Varner et al. .................. | 424/423 |
| 2006/0105015 A1 * | 5/2006 | Perla et al. .................... | 424/423 |
| 2007/0160641 A1 * | 7/2007 | Jang .............................. | 424/423 |
| 2007/0160647 A1 * | 7/2007 | Pritchard et al. .............. | 424/423 |
| 2007/0184087 A1 * | 8/2007 | Voigts et al. ................... | 424/423 |
| 2008/0195198 A1 * | 8/2008 | Asgari ........................... | 623/1.49 |
| 2009/0326638 A1 * | 12/2009 | Atanasoska et al. .......... | 623/1.15 |
| 2010/0041788 A1 * | 2/2010 | Voigts et al. ................... | 523/113 |
| 2010/0319711 A1 * | 12/2010 | Hegde et al. .................. | 128/848 |

FOREIGN PATENT DOCUMENTS

| | | |
|---|---|---|
| DE | 44 44 445 | 6/1996 |
| DE | 195 30 249 | 2/1997 |
| DE | 197 24 869 | 12/1998 |
| DE | 101 14 244 | 10/2002 |
| DE | 101 14 245 | 10/2002 |
| DE | 101 14 364 | 10/2002 |
| DE | 102 43 132 | 4/2004 |
| DE | 102 54 215 | 6/2004 |
| DE | 103 32 072 | 3/2005 |
| DE | 695 34 083 | 3/2006 |
| DE | 10 2005 002 703 | 7/2006 |
| DE | 699 35 677 | 7/2007 |
| EP | 1267752 | 1/2003 |
| EP | 1 432 562 | 8/2006 |
| EP | 1 267 725 | 1/2010 |
| WO | WO- 03/060003 | 7/2003 |
| WO | WO- 2004/096308 | 11/2004 |

OTHER PUBLICATIONS

1992 "Subclinical Infection of the Silicone Breast Implant Surface as a Possible Cause of Capsular Contracture" Charles P. Virden et al. Aesthetic Plastic Surgery vol. 16 pp. 173-179.
Mar. 2006 "Breast implant infection with *Mycobacterium fortuitum* group: Report of case and review" Donald C. Vinh et al. Journal of Infection vol. 52, Issue 3 pp. e63-e67.
May 2, 2006 "Effect of surface proteins on *Staphylococcus epidermidis* adhesion and colonization on silicone" Haiying Tang et al. Colloids and Surfaces B: Biointerfaces vol. 51 pp. 16-24.
Jul. 2007 "Clinical and Morphological Conditions in Capsular Contracture Formed around Silicone Breast Implants" Lukas Prantl, M.D., et al. Plastic and Reconstructive Surgery vol. 120, No. 1 pp. 275-284.
Jan. 19, 2003 "Implantable applications of chitin and chitosan" Eugene Khor et al. Biomaterials vol. 24 pp. 2339-2349.
Dec. 1995 "The Fate of Breast Implants: A Critical Analysis of Complications and Outcomes" Neal Handel, M.D., et al. Plastic and Reconstructive Surgery vol. 96, No. 7 pp. 1521-1533.
Jul. 10, 2006 "Construction of antibacterial multilayer films containing nanosilver via layer-by-layer assembly of heparin and chitosan-silver ions complex" Jinhong Fu et al. Antibacterial Multilayer Films Containing Nanosilver pp. 665-674.
Feb. 24, 2006 "Crosslinked chitosan implants as potential degradable devices for brachytherapy: In vitro and in vivo analysis" Abdel Kareem AZAB et al. Journal of Controlled Release vol. 111 pp. 281-289.

(Continued)

*Primary Examiner* — Suzette J Gherbi
(74) *Attorney, Agent, or Firm* — Jordan and Hamburg LLP

(57) ABSTRACT

The invention relates to a soft-tissue implant for use in the medical field which has an antibacterial effect. The soft-tissue implant, which may for example be a breast implant, has at least one antibiotic substance bound to the implant surface in first and second configurations that release the antibiotic substance, after implanting in an animal body, at short term and long term release rates. The first and second configurations are each present at one or more common surface locations. The soft-tissue implant has an antibacterial effect that prevents or reduces the deposition of bacteria and the formation of bacteria-containing biofilms.

18 Claims, No Drawings

OTHER PUBLICATIONS

May 6, 2005 "Late Infection Following Breast Augmentation with Textured Silicone Gel-Filled Implants" Antonio Roberto Basile, M.D., et al. Aesthetic Surgery Journal vol. 25, No. 3 pp. 249-254.

2006 "Capsular contracture around saline-filled and textured subcutaneously-placed implants inirradiated and non-irradiated breast cancer patients: Five years of monitoring of a prospective trial" K. Benediktsson et al. Journal of Plastic, Reconstructive & Aesthetic Surgery vol. 59 pp. 27-34.

Jun. 1995 "Characterization of Microbial Presence at the Surface of Silicone Mammary Implants" Marek K. Dobke, M.D., et al. Annals of Plastic Surgery vol. 34, No. 6 pp. 563-571.

* cited by examiner

SOFT-TISSUE IMPLANT HAVING ANTIBACTERIAL EFFECT

BACKGROUND OF THE INVENTION

The invention relates to a soft-tissue implant having antibacterial properties for use in the medical field.

Soft-tissue implants are used to fill tissue. The perhaps most known soft tissue implant is the breast implant used to increase breast size.

Breast implants normally include a polymer sheath, preferably silicone, whereby the implant is filled with silicone (highly cohesive) or an isotonic salt solution (NaCl) in order to provide the implant with properties similar, if not identical to, the living tissue that the implant augments or replaces.

Breast implants may cause different complications, e.g. infections, after the implantation. According to its intended purpose, a medical implant is placed at the location of implantation through a small, surgically created opening in the body. In this process, the implant comes inevitably in contact with the skin that surrounds the opening. As a result of bacterial contamination of the implant, an infection may occur after the operation (Vinh D. C. et. al., Breast Implant Infection with Myobacterium Fortuitum Group: Report of Case and Review, Journal of Infection 2006, Volume: 52. e63-e67). According to literature, infections occur in 9% of the operations (*Aesthetic Surg J* 2005; Volume 25, pages 249-254; Antonio Roberto Basile, M D; Filipe Basile, M D; and Arthur Volpe Dangieri Basile: Late Infection Following Breast Augmentation With Textured Silicone Gel-Filled Implants). About 2% of the infections are observed during the first 20 days after the operation and about 3% are observed during 20-288 days (on average after 82 days). Bacteria are able to build up a biofilm on implant surfaces and survive in it during an extended period of time.

Biofilms protect bacteria against antibiotics, as well. If a biofilm exists on an implant surface the bacteria can be controlled by agents beyond the biofilm but it may be that the infection spreads in the implant-containing body over a period of weeks, months, or even years.

Another problem is the increasing resistance of microorganisms against antibiotics. For this reason it makes sense to provide the implant surface with an antibacterial coating.

Apart from the existence of resistant germs, capsular contracture is another possible complication that, in the worst case, can lead to the explantation of the breast implants because the contraction of the connective tissue capsule can cause tactile sclerotizations, breast deformation and even the rupture of the silicone sheath.

About 20% of the women who have an implant suffer from capsular contracture (Benediktsson K. an Perbeck L., N Irradiated and Non-Irradiated Breast Cancer Patients: Five Years of Monitoring of a Prospective Trial, Journal of Plastic, Reconstructive & Aesthetic Surgery 2006; Volume 59, pages 27-34).

The cause of capsular contracture is not yet known. Among other reasons, a bacterial colonization of the implant has been considered (Virden C. P. et al.; Subclinical Infection of the Silicone Breast Implant Surface as a Possible Cause of Capsule Contracture, Aesth. Plast. Surg., 16 (1992) 173; Handel N. et al.; The Date of Breast Implants: A Critical Analysis of Complications and Out-Comes; Plast. Reconstr. Surg., 86 (1995) 1521; Dopke M. K. et al., Characterisation of Microbial Presence at the Surface of Silicone Mammary Implants, Ann. Plast. Surg., 34 (1995) 563; Prantl L. et al.; Clinical and Morphological Conditions in Capsular Contracture Formed Around Silicone Breast Implants, Plast. Reconstr. Surg., 120 (2007) 275-284).

The most frequent type of breast implant procedure takes place to increase the size of the breast. Less frequently, the implant is inserted to augment the breast after tumor removal. Normally, the implant consists of a sheath of silicone, seldom of polyurethane, filled with silicone, isotonic salt solution, soybean oil (that was already taken from the market) or other liquids such as collagen solution (see DE 195 30 249 A1) to give the implant consistency that is similar to the breast tissue.

The production of breast implants by machines is known, for example, from EP 1 432 562 B1). The manufacture of specific geometries is disclosed in EP 1 267 725 B1.

DE 695 34 083 T2 introduces a breast implant with autologous cells in a polymer matrix based on a hydrogel. The use of metal ions with an antibiotic effect has been known for quite a long time.

Metal ion complexes formed between at least one metal ion and an organic complexing agent have also been known for a long time. Calcium ions, for example, complex with ethylenediaminetetraacetate (EDTA) in coagulation examinations. Apart from molecules such as EDTA, certain polymers or polysaccharides are known to have functional groups used to form complexes. Carboxyl groups and amino groups have a complexing effect for polysaccharides; usually polysaccharides that contain amino groups are used.

The use of metal ion/polysaccharide complexes has not only been described in technical applications but also in medicine. For example, a chitosan-copper complex is used in tumor treatment because of its increased activity compared to uncomplexed copper ions (Yong Zheng et al.; Preparation of Chitosan-Copper Complexes and their Antitumor Activity; Bioorganic & Medicinal Chemistry Letters 16 (2006) 4127-4129).

It is also known that implantable systems of chitin and chitosan can selectively release active substances if the pH-value is changed. This change can be realized, for example, by a kind of controllable membrane made of these materials (Eugene Khor and Lee Yong Lim; Implantable Applications of Chitin and Chitosan; Biomaterials 24 (2003) 2339-2349).

Moreover, diverse coatings of implants having an antibacterial effect are known.

Well-known procedures such as the change of the hydrophobicity/hydrophilicity, the use of smooth or structured surfaces have already been examined.

In WO 2004/096308, for example, a metal coating on the outer side of the silicone sheath of breast implants is described.

Coatings of polysaccharides, such as chitosan and chitosan derivatives for the surface coating of implants and medical instruments, are disclosed in DE 197 24 869 A1. Other polysaccharide coatings are disclosed, for example, in DE 44 44 445 C2.

WO 03/060003 A1 describes the production process of plastics articles (thermoplastics) for consumer goods by extrusion (injection molding) in which a metal-chitosan complex with antibacterial effect is added to the polymer mass.

An antibacterial film has been generated by a polysaccharide coating that contains silver nano-particles (Jinhong Fu et al.; Construction of Antibacterial Multilayer Films Containing; Journal of Biomedical Materials Research Part A, Volume 79A, 3 (2006) 665-674).

An antibacterial effect can also be produced for silicone implants by increasing the hydrophobicity. This effect is achieved by a surface silanization or polysaccharide coating without metal ions or active substances (H. Tang et al.; Effect of Surface Modification of Silicone on *Staphylococcus* Epidermidis Adhesion and Colonization; Colloids and Surfaces B: Biointerfaces 51 (2006) 16-24).

A completely absorbable implant is produced by the cross-linking of chitosan with glutaraldehyde. By the addition of radioactive iodine a local radiation can be realized for brachytherapies. (Abdel Kareem Azab et al.; Crosslinked Chitosan Implants as Potential Degradable Devices for Brachytherapy: In Vitro and in Vivo Analysis; Journal of Controlled Release 11 (2006) 281-289).

Another kind of coating is described in DE 102 43 132 B4. Here, copper ions are released from a copper-containing titanium dioxide layer that is applied on implants. This layer is produced by metal-organic titanic oxide precursors and its formation requires a thermal conversion.

Agent-releasing systems that release antibiotic substances are also known for implants. DE 1023 32 072 B4, for example, describes an individually adjustable agent-releasing system. Here, an implantable carrier is provided with several openings in which the agents of different types are introduced. In this system, the active agents are released locally in a small region. For example, this implant, filled with antibiotics, can be screwed into the inflamed opening after the removal of an external fixation. This technique does not allow a large-surface and uniform release of agents, e.g. the generation of an antibacterial surface on a breast implant.

DE 10 2005 002 703 A1 discloses an antibiotic coating of implants that consists at least of one saturated, organic, hydrophobic, low-molecular matrix former that has a melting point in the temperature range from 45° C. to 100° C. and a low-molecular, hydrophobic additive is dissolved in it. An antibiotic/antibiotic is suspended in the mixture of the matrix former and additive and/or an antibiotic/antibiotics that can be mixed with the mixture of the matrix former and additive is dissolved in it.

DE 102 54 215 A1 describes a surgical, antimicrobial implant with a basic structure and at least a partial coating. The implant has alpha-hydroxycarboxylic acid oligomers (preferentially lactic acid oligomers) and/or allows them to develop as a degradation product after the implantation. The coating contains polyol fatty acid monoester, preferably glycerol fatty acid monoester.

In DE 101 14 364 A1, a method for the production of antibiotic compositions is explained. In this method a plastically deformable salt, which is built up of at least one cationic component of a protonized antibiotic base from the groups of the amino glycoside antibiotics, the lincosamide antibiotics and the tetracycline antibiotics and of at least one anionic component of the group of the organic sulfates and/or organic sulfonates and/or fatty acid esters, is used for the fixation of the inorganic composite components and/or organic composite components and, possibly by the addition of water, for the formation of the composites, particularly by pressing, extruding, rolling, calendaring and milling processes.

DE 101 14 245 A1 describes the production and use of an antibiotic/antibiotics preparation for human and veterinary medicine for the treatment of local microbial infections in hard and soft tissues. According to this invention, an antibiotic/antibiotics preparation is produced by mixing water, an amphiphilic component of a representative of the alkylsulfates, arylsulfates, alkylaryl sulfates, cycloalkyl sulfates, alkylcycloalkyl sulfates, alkyl sulfamates, cycloalkyl sulfamates, alkylcycloalkyl sulfamates, aryl sulfamates, alkylaryl sulfamates, alkyl sulfonates, fatty acid-2-sulfonates, aryl sulfonates, alkylaryl sulfonates, cycloalkyl sulfonates, alkylcycloalkyl sulfonates, alkyl bisulfates, cycloalkyl bisulfates, alkyl bisulfonates, cycloalkyl bisulfonates, aryl bisulfonates, alkylaryl bisulfonates, aryl trisulfonates and alkylaryl trisulfonates, one or more antibiotic components from the group of the aminoglycoside antibiotics, the lincosamide antibiotics and tetracycline antibiotics, an organic auxiliary component and/or an inorganic auxiliary component and, possibly, at least one biologically active auxiliary component and this mixture is formed to molded bodies, granulated materials, powders, films, fleeces and threads.

DE 101 14 244 A1 discloses an antibiotic/antibiotics preparation for absorbable and non-absorbable implants for human and veterinary medicine for the treatment of local microbial infections in hard and soft tissues. This antibiotic/antibiotics preparation is a mixture consisting of at least one amphiphilic component of a representative of the alkyl sulfates, aryl sulfates, alkylaryl sulfates, cycloalkyl sulfates, alkylcycloalkyl sulfates, alkyl sulfamates, cycloalkyl sulfamates, alkylcycloalkyl sulfamates, aryl sulfamates, alkylaryl sulfamates, alkyl sulfonates, fatty acid-2-sulfonates, aryl sulfonates, alkylaryl sulfonates, cycloalkyl sulfonates, alkylcycloalkyl sulfonates, alkyl bisulfates, cycloalkyl bisulfates, alkyl bisulfonates, cycloalkyl bisulfonates, aryl bisulfonates, alkylaryl bisulfonates, aryl trisulfonates and alkylaryl trisulfonates and of at least one antibiotic components from the group of the aminoglycoside antibiotics, the lincosamide antibiotics or tetracycline antibiotics and, possibly, at least of one waterless organic auxiliary component and, possibly, of at least one inorganic auxiliary component and, possibly, of at least one biologically active auxiliary component. This inventive antibiotic/antibiotics preparation exhibits a delayed release of the active agents.

DE 699 35 677 T2 describes an antibiotic hydrophilic coating.

US 2003/0203003 A1 discloses a degradable implant consisting of fibers that are filled with agents. By weaving two different fibers different agents can be released or within one fiber different agents can be released in different regions. In this technical solution the agent can be released across a surface.

US 2007/0160641 A1 discloses a stent used for a medical device. Here, a layer structure with two regions of different release kinetics or several layers can be provided.

DE 102 43 132 B4 discloses a method for the production of a biocompatible metal-ion-containing titanium oxide coating on an implant. The metal ions can be eluted under physiological conditions, are homogeneously distributed in the coating and can have an antibiotic effect. According to this method, the $TiO_2$ coating is applied at a temperature ranging from 100 to 1000° C. and an inner layer can consist of Cu or Ag so that, depending on the ions, different release kinetics can exist.

SUMMARY OF THE INVENTION

The invention provides a soft-tissue implant, for example a breast implant, having an antibacterial effect that avoids the disadvantages of the prior art, in that the bacterial contamination of implants, particularly breast implants, as a result of the deposition of bacteria and the formation of biofilms, is prevented and/or reduced.

The soft-tissue implant of the present invention, for example, a breast implant, has antibiotic substances bound on said implant to a surface thereof, in at least one short term and one long term release mechanism region, i.e., sites where the antibiotic substances are bound to the implant surface in short-term and long term release configurations. After implanting, the antibiotic substances are released in the mammal at different release rates, i.e., short term release and long term release, or by different release mechanisms. By means of this mechanism one or several different antibiotic substances can be released.

Consequently, not only a local but a surface release of the agent concentration is achieved over the whole implant by this invention so that only low agent concentrations are required.

Furthermore, the short term release of antibiotic substances inhibits the primary deposition of bacteria and the long term release of antibiotic substances combats the remaining, surviving bacteria so that biofilm formation is prevented.

Due to the inventive combination of short-term and long-term releases, antibiotic substances are released shortly after implanting, and an effective concentration (between MIN and MAX) of antibiotic substance is achieved and maintained for a longer period. Moreover, a maximum concentration (MAX) is not exceeded because short term release is provided for.

The different concentrations of short term and long term releases are realized via different release mechanisms (e.g. adsorption-desorption, diffusion, ion exchange, matrix degradation, and others) and/or via different spatially separated designs (e.g. layer construction, amongst others).

According to the invention, different release kinetics can be selected for the release of active agents and/or ions.

The antibiotic effect of metal ions is particularly useful here.

The advantage of this invention is given by the fact that the agents are released across the whole implant surface and not only locally in one region. In case of a large implant surface a local release would cause too high local concentrations that should distribute themselves uniformly around the implant. Certainly, implants can be immersed in agents or agent solutions according to the state of the art and thus the release can also be realized across a surface but it cannot be adjusted with respect to time.

The invention is described in detail by different embodiments without being restricted to them.

DETAILED DESCRIPTION OF THE INVENTION

The present invention shall be explained through the following examples, set forth in Embodiments 1 to 5 set forth below.

Embodiment 1

Stratified, i.e., Layered Structure

A breast implant with silicone sheath is covalently coated by a reaction with a heterobi-functional azide (photochemical coupling) and the subsequent coupling of a polysaccharide (chitosan and/or heparin). An aqueous-based copper solution is brought into contact with the surface and thus the copper ions are complexed by the polysaccharide (release system F1). Afterwards, the implant is immersed into a saturated solution of acetate of copper (organic solvent, e.g. acetone). The solvent acts as a thickening agent for the silicone material and makes the penetration of the copper salt into the silicone surface possible (release system F2). The release of F1 is achieved by the ion exchange (short term release) whereas F2 is realized by the diffusion of copper ions from the silicone (long term release). It should be understood from the above that an antibiotic substance is bound to the surface of the implant in a short term release configuration and in a long term release configuration, and that the first and second configurations are present at one or more common surface locations. Specifically, the configurations are present on the surface in a layered arrangement at one or more common surface locations.

Embodiment 2

Release from a Matrix

A breast implant having a silicone sheath is covalently functionalized by a reaction with a heterobi-functional azide (photochemical coupling). Chitosan is covalently coupled to the amino group of the azide via glutaraldehyde.

A polysaccharide matrix is coupled to a part of the amino groups of the chitosan. This matrix is built up by alginic acid and chitosan. The carboxyl groups of the alginic acid are activated by a water-soluble carbodiimide so that they can be covalently coupled with the amino groups of the chitosan. The matrix can be built up either in layers (surface-glutaraldehyde-chitosan-alginic acid-chitosan-alginic acid, etc.) or by a one pot reaction in which chitosan is cross-linked with activated alginic acid in one reaction step forming the matrix.

If the matrix is rinsed with a copper solution the copper ions of the chitosan will be complexed by the excess amino groups of the chitosan not used for the cross-linking (F1) and by the excess carboxyl groups of the alginic acid that are not used for the cross-linking (F2). It should be understood from the above that an antibiotic substance is bound to the surface of the implant in a short term release configuration and in a long term release configuration, and that the first and second configurations, which result from the complexing of copper ions with the amino and carboxyl functional groups of the polysaccharides, are present at one or more common surface locations.

Embodiment 3

Release from a Matrix

An implant coated with chitosan is produced according to embodiment 1. Afterwards, a matrix consisting of polyaspartic acid and chitosan is generated by ionic links on the surface. The matrix is produced by a stratified structure of polyaspartic acid and chitosan by immersing the implant alternately in the corresponding solution. The matrix is saturated with a copper-ion-containing solution. The different release rates are achieved by the different complexion points (carboxyl group of the polyaspartic acid (F1) and of the amino group of the chitosan (F2)). It should be understood from the above that an antibiotic substance is bound to the surface of the implant in a short term release configuration and in a long term release configuration, and that the first and second configurations are present at one or more common surface locations.

Embodiment 4

The surface of a silicone implant is carboxylated by an acrylic acid graft polymerization. Then, the implant is immersed into a saturated solution of copper acetate in an organic solvent (e.g. acetone). The solvent acts as a thickening agent for the silicone material and allows the penetration of the copper salt into the silicone surface (F2). Afterwards, the implant is immersed into an aqueous copper-ion-containing solution to complex the copper ions to the carboxyl groups.

The release of F1 is achieved by the ion exchange at the carboxyl groups (short term release) whereas F2 is realized by the diffusion of copper ions from the silicone (long term release). It should be understood from the above that an antibiotic substance is bound to the surface of the implant in a short term release configuration and in a long term release configuration, and that these configurations are present at one or more common surface locations.

Embodiment 5

An active implant (e.g. a cardiac pacemaker, defibrillator, hearing aid, drug pump or inner ear prosthesis), i.e. an implantable electronic device with or without power supply, or a part or parts of an active implant is/are coated with a polymer (preferably silicone) by immersion technique.

The polymer surface is further treated according to one or several of the embodiments 1 to 4.

All elements presented in the description, the embodiments, and the subsequent claims can be essential for the invention both as single elements and in any combination.

The invention claimed is:

1. A soft-tissue implant for implanting in a mammal, the implant releasing an antibiotic substance after implanting, comprising:
    an implant having a surface,
    a first antibiotic substance bound to the surface in a first configuration that releases the first antibiotic substance according to a first release rate;
    a second antibiotic substance bound to the surface in a second configuration that releases the second antibiotic substance according to a second release rate;
    the first release rate being a short term release rate and the second release rate being a long term release rate;
    the first antibiotic substance and the second antibiotic substance being released after implanting the implant in a mammal;
    the first antibiotic substance bound to the surface in a first configuration and the second antibiotic substance bound to the surface in a second configuration each being present at a common surface location of the surface, wherein in the first configuration the first antibiotic substance comprises copper ions present in a polysaccharide complex that is coupled to the surface of the implant, and in the second configuration the second antibiotic substance comprises copper ions penetrated into the surface of the implant.

2. The soft-tissue implant of claim 1, wherein the surface is entirely covered by the first antibiotic substance bound to the surface in a first configuration and the second antibiotic substance bound to the surface in a second configuration.

3. The soft-tissue implant of claim 1, wherein the implant comprises a degradable material.

4. The soft-tissue implant of claim 1, wherein the implant is a breast implant.

5. The soft-tissue implant of claim 1, wherein the implant comprises a non-degradable silicone material.

6. The soft-tissue implant of claim 1, wherein the implant is an expander prosthesis.

7. The soft-tissue implant of claim 1, wherein the implant is a functioning medical device.

8. The soft-tissue implant of claim 7, wherein the functioning medical device is selected from the group consisting of a heart pacemaker, a defibrillator, a drug pump, and an inner ear prosthesis.

9. The soft-tissue implant of claim 1, wherein the implant is comprised of a non-degradable material.

10. The soft-tissue implant of claim 1, wherein the first antibiotic substance bound to the surface in a first configuration and the second antibiotic substance bound to the surface in a second configuration are each present at a plurality of common surface locations of the surface.

11. The soft-tissue implant of claim 1, wherein each of the first antibiotic substance bound to the surface in a first configuration and the second antibiotic substance bound to the surface in a second configuration entirely cover the surface.

12. A soft-tissue implant for implanting in a mammal, the implant releasing an antibiotic substance after implanting, comprising:
    an implant having a surface;
    a first antibiotic substance bound to the surface in a first configuration that releases the first antibiotic substance according to a first release rate;
    a second antibiotic substance bound to the surface in a second configuration that releases the second antibiotic substance according to a second release rate;
    the first release rate being a short term release rate and the second release rate being a long term release rate;
    the first antibiotic substance and the second antibiotic substance being released after implanting the implant in a mammal;
    the first antibiotic substance bound to the surface in a first configuration and the second antibiotic substance bound to the surface in a second configuration each being present at a common surface location of the surface, wherein in the first configuration, the first antibiotic substance comprises copper ions complexed with chitosan, and in the second configuration the second antibiotic substance comprises copper ions complexed with alginic acid, the chitosan and alginic acid comprising a polysaccharide matrix coupled to a chitosan linker that is coupled to the surface of the implant.

13. A soft-tissue implant for implanting in a mammal, the implant releasing an antibiotic substance after implanting, comprising:
    an implant having a surface,
    a first antibiotic substance bound to the surface in a first configuration that releases the first antibiotic substance according to a first release rate;
    a second antibiotic substance bound to the surface in a second configuration that releases the second antibiotic substance according to a second release rate;
    the first release rate being a short term release rate and the second release rate being a long term release rate;
    the first antibiotic substance and the second antibiotic substance being released after implanting the implant in a mammal;
    the first antibiotic substance bound to the surface in a first configuration and the second antibiotic substance bound to the surface in a second configuration each being present at a common surface location of the surface, wherein in the first configuration the first antibiotic substance comprises copper ions complexed with polyaspartic acid, and in the second configuration the second antibiotic substance comprises copper ions complexed with chitosan, the polyaspartic acid and chitosan comprising a matrix coupled to the surface of the implant.

14. A soft-tissue implant for implanting in a mammal, the implant releasing an antibiotic substance after implanting, comprising:
    an implant having a surface grafted with an acrylic acid polymer to provide carboxyl groups at the implant surface;
    a first antibiotic substance bound to the surface in a first configuration that releases the first antibiotic substance according to a first release rate;

a second antibiotic substance bound to the surface in a second configuration that releases the second antibiotic substance according to a second release rate;

the first release rate being a short term release rate and the second release rate being a long term release rate;

the first antibiotic substance and the second antibiotic substance being released after implanting the implant in a mammal;

the first antibiotic substance bound to the surface in a first configuration and the second antibiotic substance bound to the surface in a second configuration each being present at a common surface location of the surface, wherein in the first configuration the first antibiotic substance comprises copper ions complexed with the carboxyl groups and in the second configuration the second antibiotic substance comprises copper ions that are embedded in the surface of the implant.

15. A soft-tissue implant of claim 1 wherein the surface of the implant is provided with a silicone coating prior to providing the implant with the first antibiotic substance bound to the surface in the first configuration and the second antibiotic substance bound to the surface in the second configuration.

16. A soft-tissue implant of claim 12 wherein the surface of the implant is provided with a silicone coating prior to providing the implant with the first antibiotic substance bound to the surface in the first configuration and the second antibiotic substance bound to the surface in the second configuration.

17. A soft-tissue implant of claim 13 wherein the surface of the implant is provided with a silicone coating prior to providing the implant with the first antibiotic substance bound to the surface in the first configuration and the second antibiotic substance bound to the surface in the second configuration.

18. A soft-tissue implant of claim 14 wherein the surface of the implant is provided with a silicone coating prior to providing the implant with the first antibiotic substance bound to the surface in the first configuration and the second antibiotic substance bound to the surface in the second configuration.

* * * * *